United States Patent [19]

Michálek

[11] Patent Number: 5,045,323

[45] Date of Patent: Sep. 3, 1991

[54] COMPOUND AND METHOD OF PREPARING COMPOUND FOR MEDICAL PURPOSES FROM EGGSHELLS

[75] Inventor: Karol Michálek, Trnava, Czechoslovakia

[73] Assignee: Zäpadoslovanské hydinärske závody štátny podnik, Trnava, Czechoslovakia

[21] Appl. No.: 371,427

[22] Filed: Jun. 26, 1989

[30] Foreign Application Priority Data

Jun. 24, 1988 [CS] Czechoslovakia .............. PV4454-88

[51] Int. Cl.$^5$ ..................... A61K 33/42; A61K 33/06; A61K 33/10
[52] U.S. Cl. .................................. 424/601; 424/682; 424/686; 424/602; 424/687; 424/581
[58] Field of Search ................. 424/601, 682, 95, 687, 424/686, 602

[56] References Cited

PUBLICATIONS

Chem Abst. 90:66501d, vol. 90 (1979), Trnouec et al.

Primary Examiner—Frederick E. Waddell
Assistant Examiner—Zohreh A. Fay
Attorney, Agent, or Firm—Notaro & Michalos

[57] ABSTRACT

Eggshells are utilized after preliminary treatment for medical purposes for treating certain diseases and to compensate for deficiencies of mineral in living tissues, particularly in bone tissues in a form which is acceptable by the body.

6 Claims, No Drawings

COMPOUND AND METHOD OF PREPARING COMPOUND FOR MEDICAL PURPOSES FROM EGGSHELLS

FIELD AND BACKGROUND OF THE INVENTION

The invention relates to a method for utilizing eggshells, particularly of chicken eggs, for medical purposes and to a compound obtained from eggshells.

Eggshells contain a number of constituents including calcium, phosphorus, magnesium and a number of trace elements in a biogenous bonding system.

The present pharmaceutical industry utilizes mostly anorganic raw materials for preparation of different medicaments. Medicaments prepared from anorganic raw materials either lack certain elements or contain these elements in conditions which do not enable their full medical utilization. At present there is no really effective medicament which could be applied for curing certain diseases, particularly osteoporosis, coxarthrosis and the like, prepared on the basis of organically-biologically transformed and synthesized minerals and of trace elements with a proteinaceous bonding.

So far eggshells have been used for curing certain diseases. Their application has been based on intuition without determination of their proper effectiveness based on objective biological knowledge.

SUMMARY OF THE INVENTION

It is an object of this invention to provide a method of preparing compounds from eggshells, particularly from chicken eggshells, which could be effectively utilized for medical purposes for treating certain diseases and for replacement of certain deficient materials in living tissues, which would be accepted by the body for full utilization and also to provide compounds of certain elements in a proteinaceous bonding system.

The compound of the invention is capable of fully balancing deficient biogenous mineral compounds and trace elements when treating, for instance, different diseases such as osteopatia and chondropatia and other diseases of bones where remineralization is required, as in osteoporosis, coxarthrosis and where an increase in the speed of creation of callus is required. Remedies actually used in connection with similar diseases based on anorganic compounds are generally little effective and for geriatic patients substantially without success and frequently end lethally.

The speed and efficiency of metabolization of the inventive compound has been checked by pharmacokinetic methods and by observing the subjective improvement of a patient. Also a roentgenologic and densitometric investigation of the conditions of the whole skeleton or of local fractures and of changes of joints, of the condition of the spine and of different bone tissues has been checked. The efficiency of application of remedies according to this invention proved particularly effective for geriatric patients where currently used remedies have not been effective, or have caused unfavorable subsidiary effects, or have not been properly tolerated by the body. The most effective application of the product has proved to be in powder form.

The method for preparation of a compound from eggshells for medical purposes will be described in detail in the following.

DESCRIPTION OF THE PREFERRED EMBODIMENT

To prepare the compound of the present invention, chicken eggshells are first separated from their contents of white and yolk, and then treated on a centrifuged separator in order to remove any remaining white. The centrifuged shells are washed in water to remove the rest of the white, to remove the film sticking to the internal part of the shell and to remove other contaminants. The shells are subsequently rinsed with clean water. The water is then removed advantageously by a centrifugal separator with a following drying treatment using hot air at a temperature of up to 150° C., advantageously between 60° and 120° C. This is followed by crushing and grinding to a fine powder of a particle size of up to 150 microns, advantageously between 10 and 80 microns. The powder is then sieved and subsequently sterilized in order to devitalize pathogenous and conditionally pathogenous microorganisms. The sterilization should proceed for about one hour at a temperature about 120° C. The finished product should be checked for possible traces of microorganisms.

The thus obtained powder comprises substantially the following biologically bonded elements:

calcium:30.0 to 40.0 g/100 g of powder and other biogenous elements in addition to trace elements such as:

magnesium:0.35 to 0.5 g/100 g of powder
phosphorus:about 0.08 g/100 g of powder
carbonates:46.0 to 60.0 g/100 g powder
nitrogen:0.5 to 0.6 g/100 g powder.

The resulting compound can be utilized in the following branches of medical indications: pediatry, traumatology, geriatry, orthopedy, stomatology, puerperium, oncology, pneumopathy.

While a specific embodiment of the invention has been shown and described in detail to illustrate the application of the principles of the invention, it will be understood that the invention may be embodied otherwise without departing from such principles.

What is claimed is:

1. A method of preparing a composition for medical purposes involving deficiencies of minerals in bone tissues, comprising:
    removing the contents of eggshells which include egg white and egg yolk, from the eggshells;
    subjecting the eggshells to centrifugal separation to remove additional egg white from the shells;
    subsequently washing the eggs shells in water to remove any additional egg white, a sticky film from interior surfaces of the eggshells, and other contaminants;
    rinsing the washed eggshells with clear water;
    subjecting the washed and rinsed eggshells to centrifugal separation to remove the eggshells from the water;
    drying the eggshells which have been separated from the water using hot air;
    crushing the dried eggshells;
    grinding the crushed eggshells to a powder having a particle size smaller than 150 microns; and
    sterilizing the eggshell powder at sufficiently high temperature to devitalize pathogenous and conditionally pathogenous microorganisms.

2. A method according to claim 1 including drying the eggshells using hot air at a temperature up to 150° C.

3. A method according to claim 2 wherein the temperature is between 60° and 120° C.

4. A method according to claim 3 including sterilizing the powder at a temperature of about 120° C. for about one hour.

5. A method according to claim 4 including grinding the crushed eggshells to a particle size of 10 to 80 microns.

6. A method according to claim 1 including grinding the crushed eggshells to a particle size of 10 to 80 microns.

* * * * *